United States Patent
Mjalli et al.

(10) Patent No.: US 10,364,233 B2
(45) Date of Patent: Jul. 30, 2019

(54) PIPERIDINE DERIVATIVE AND METHODS OF USE THEREOF

(71) Applicant: vTv Therapeutics LLC, High Point, NC (US)

(72) Inventors: Adnan M. M. Mjalli, Oak Ridge, NC (US); Anitha Hari, High Point, NC (US); Bapu Gaddam, Ellicott City, MD (US); Daniel P. Christen, Jamestown, NC (US); Dharma Rao Polisetti, High Point, NC (US); William Kenneth Banner, Greensboro, NC (US); Raju Bore Gowda, Brentwood, CA (US); Robert Carl Andrews, Jamestown, NC (US); Suparna Gupta, Greensboro, NC (US)

(73) Assignee: vTv Therapeutics LLC, High Point, NC (US)

( * ) Notice: Subject to any disclaimer, the term of this patent is extended or adjusted under 35 U.S.C. 154(b) by 0 days.

(21) Appl. No.: 16/109,224

(22) Filed: Aug. 22, 2018

(65) Prior Publication Data

US 2018/0362505 A1    Dec. 20, 2018

Related U.S. Application Data

(63) Continuation of application No. PCT/US2017/019050, filed on Feb. 23, 2017.

(60) Provisional application No. 62/301,748, filed on Mar. 1, 2016.

(51) Int. Cl.
*C07D 401/14* (2006.01)

(52) U.S. Cl.
CPC .................. *C07D 401/14* (2013.01)

(58) Field of Classification Search
CPC ................................................... C07D 401/14

USPC ......................................................... 514/316
See application file for complete search history.

(56) References Cited

FOREIGN PATENT DOCUMENTS

| WO | WO 2011/041198 | 4/2011 |
| WO | WO 2011/103091 | 8/2011 |

OTHER PUBLICATIONS

Giuseppe Verdile et al. The role of beta amyloid in Alzheimer's disease. (Year: 2004).*
Amendment No. 6 to Form S-1 Registration Statement for vTv Therapeutics Inc., Jul. 24, 2015. pp. 1-2, 83, 86-94.
Burstein A, et al. "Azeliragon Phase 2b Survival Analysis Supports Beneficial Effects on Delaying Time to Cognitive Deterioration in Patients with Mild Alzheimer's Disease." Poster Presented at the Alzheimer's Association International Conference. Jul. 27, 2016. Toronto, Canada.
Investor Presentation—Jul. 2015. Slides 9-18.
Sabbagh M, et al. "Safety and efficacy results from the phase 3, multicenter, 18-month STEADFAST trial of azeliragon in participants with mild Alzheimer's disease." Presented at 2018 CTAD. Oct. 26, 2018. Barcelona, Spain.

* cited by examiner

*Primary Examiner* — Rita J Desai
(74) *Attorney, Agent, or Firm* — Samuel B. Rollins

(57) ABSTRACT

The present invention provides N-[1-(1-Cyclohexyl-3,5-dimethyl-1H-pyrazole-4-sulfonyl)-4-phenyl-piperidin-4-ylmethyl]-N-isobutyl-4-{[(piperidin-4-ylmethyl)-amino]-methyl}-benzenesulfonamide and pharmaceutically acceptable salts thereof. These compounds may be useful in the treatment of diseases such as Alzheimer's disease or renal failure. The present invention further relates to methods for the preparation of compounds of Formula (I) and pharmaceutically acceptable salts thereof, pharmaceutical compositions comprising such compounds, and the use of such compounds and/or pharmaceutical compositions in treating certain diseases.

6 Claims, No Drawings

PIPERIDINE DERIVATIVE AND METHODS OF USE THEREOF

FIELD OF THE INVENTION

This invention relates to a compound that is an inhibitor of the interaction between the receptor for advanced glycation endproducts (RAGE) and its physiological ligands such as advanced glycated end products (AGEs), S100/calgranulin/EN-RAGE, β-amyloid, and amphoterin, for the treatment of RAGE mediated diseases.

BACKGROUND OF THE INVENTION

The Receptor for Advanced Glycated Endproducts (RAGE) is a member of the immunoglobulin super family of cell surface molecules. RAGE is expressed in most tissues, and in particular, is found in cortical neurons during embryogenesis. Increased levels of RAGE are also found in aging tissues, and the diabetic retina, vasculature and kidney. Activation of RAGE in different tissues and organs leads to a number of pathophysiological consequences. RAGE has been implicated in a variety of conditions including: acute and chronic inflammation, the development of diabetic late complications such as increased vascular permeability, nephropathy, atherosclerosis, and retinopathy. RAGE has also been implicated in Alzheimer's disease, erectile dysfunction, and in tumor invasion and metastasis.

Advanced glycation endproducts (AGEs) have been implicated in a variety of disorders including complications associated with diabetes and normal aging. Incubation of proteins or lipids with aldose sugars results in nonenzymatic glycation and oxidation of amino groups on proteins to form Amadori adducts. Over time, the adducts undergo additional rearrangements, dehydrations, and cross-linking with other proteins to form complexes known as AGEs. Factors which promote formation of AGEs include delayed protein turnover (e.g. as in amyloidoses), accumulation of macromolecules having high lysine content, and high blood glucose levels (e.g. as in diabetes).

AGEs display specific and saturable binding to cell surface receptors on endothelial cells of the microvasculature, monocytes and macrophages, smooth muscle cells, mesengial cells, and neurons.

In addition to AGEs, other compounds can bind to, and inhibit the interaction of physiological ligands with RAGE. In normal development, RAGE interacts with amphoterin, a polypeptide which mediates neurite outgrowth in cultured embryonic neurons. RAGE has also been shown to interact with β-amyloid.

Binding of ligands such as AGEs, S100/calgranulin/EN-RAGE, β-amyloid, CML (Nε-Carboxymethyl lysine), and amphoterin to RAGE has been shown to modify expression of a variety of genes. For example, in many cell types interaction between RAGE and its ligands generates oxidative stress, which thereby results in activation of the free radical sensitive transcription factor NF-κB, and the activation of NF-κB regulated genes, such as the cytokines IL-1β, TNF-α, and the like.

In addition, several other regulatory pathways, such as those involving p21ras, MAP kinases, ERK1 and ERK2, have been shown to be activated by binding of AGEs and other ligands to RAGE. In fact, transcription of RAGE itself is regulated at least in part by NF-κB. Thus, an ascending, and often detrimental, spiral is fueled by a positive feedback loop initiated by ligand binding. Inhibiting binding of physiological ligands to RAGE provides for the down-regulation of the pathophysiological changes brought about by excessive concentrations of AGEs and other ligands for RAGE as described above.

Thus, there is a need for the development of compounds that inhibit the binding of physiological ligands to RAGE.

SUMMARY OF THE INVENTION

The present invention relates to a compound of Formula (I):

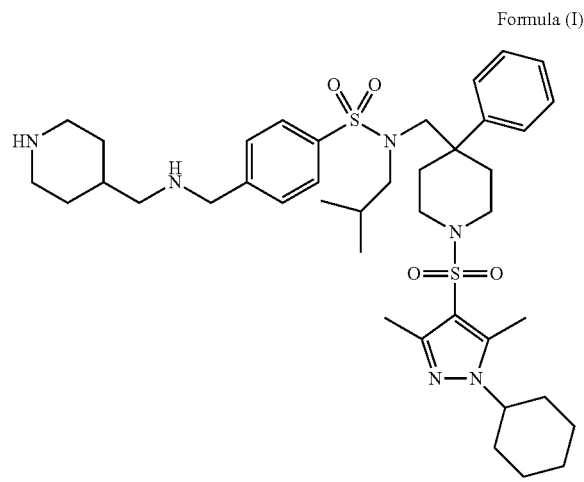 [SMILES: Cc1nn(C2CCCCC2)c(C)c1S(=O)(=O)N1CCC(CN(CC(C)C)S(=O)(=O)c2ccc(CNCC3CCNCC3)cc2)(c2ccccc2)CC1]

Formula (I)

or pharmaceutically acceptable salts thereof as described herein. The compound of Formula (I) is referred to as N-[1-(1-Cyclohexyl-3,5-dimethyl-1H-pyrazole-4-sulfonyl)-4-phenyl-piperidin-4-ylmethyl]-N-isobutyl-4-{[(piperidin-4-ylmethyl)-amino]-methyl}-benzenesulfonamide.

This invention also provides for methods of preparing a compound of Formula (I) or pharmaceutically acceptable salts thereof, pharmaceutical compositions comprising a compound of Formula (I) or a pharmaceutically acceptable salt thereof; and methods for the use of a compound of Formula (I) or pharmaceutically acceptable salt thereof in treating diseases mediated by RAGE. This invention also provides use of a compound of Formula (I) or a pharmaceutically acceptable salt thereof in preparation of a medicament. This invention also provides for use of a compound of Formula (I) or a pharmaceutically acceptable salt thereof in preparation of a medicament for treatment of one or more of the conditions listed below.

A compound of Formula (I) or a pharmaceutically acceptable salt thereof is useful as an inhibitor of the interaction of the receptor for advanced glycation endproducts (RAGE) with ligands such as advanced glycated end products (AGEs), S100/calgranulin/EN-RAGE, β-amyloid, and amphoterin. The compounds may also be useful in treating a variety of diseases or conditions in humans that may be responsive to the inhibition of RAGE. Such diseases or conditions include, but are not limited to, acute and chronic inflammation, the development of diabetic late complications such as increased vascular permeability, nephropathy, atherosclerosis, and retinopathy, the development of Alzheimer's disease and related disorders, erectile dysfunction, tumor invasion and metastasis, and osteoporosis.

The scope of the present invention also includes combinations of the various aspects, embodiments, and preferences as herein described.

DETAILED DESCRIPTION OF THE INVENTION

The present invention provides to a compound of Formula (I):

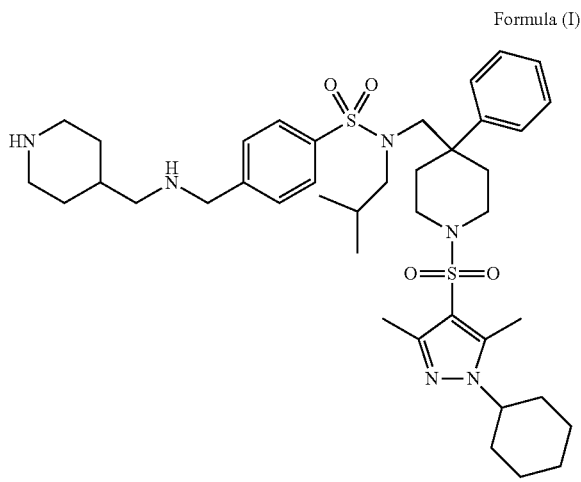 [SMILES: Cc1nn(C2CCCCC2)c(C)c1S(=O)(=O)N1CCC(CN(CC(C)C)S(=O)(=O)c2ccc(CNCC3CCNCC3)cc2)(c2ccccc2)CC1]

Formula (I)

or a pharmaceutically acceptable salt thereof. In another embodiment, the present invention provides a hydrochloride salt of a compound of Formula (I). In another embodiment, the present invention provides a dihydrochloride salt of a compound of Formula (I).

Another embodiment of the present invention includes a pharmaceutical composition comprising a compound of Formula (I) or a pharmaceutically acceptable salt thereof and a pharmaceutically acceptable carrier.

One embodiment of the present invention includes a method for treating a RAGE-mediated disease comprising administering to a subject a compound of Formula (I) or a pharmaceutically acceptable salt thereof.

This invention also provides use of a compound of Formula (I) or a pharmaceutically acceptable salt thereof in preparation of a medicament. This invention also provides for use of a compound of Formula (I) or a pharmaceutically acceptable salt thereof in preparation of a medicament for treatment of one or more of the conditions listed below. Another embodiment includes use of a compound of Formula (I) or a pharmaceutically acceptable salt thereof for the manufacture of a medicament for treating a RAGE-mediated disease. A still further embodiment includes a compound of Formula (I) or a pharmaceutically acceptable salt thereof for use in the treatment of a RAGE-mediated disease. In one embodiment, the disease is Alzheimer's Disease. In one embodiment, such treatment modifies the presentation of Alzheimer's Disease. In another embodiment, such treatment improves cognitive performance of a subject suffering from mild to moderate Alzheimer's Disease.

The term "pharmaceutically acceptable salt(s)" as used herein refers to non-toxic salts of a compound of Formula (I) which are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isethionate, Lactate, Lactobionate, Laurate, Malate, Maleate, Mandelate, Mesylate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. When an acidic substituent is present, such as —COOH, there can be formed the ammonium, morpholinium, sodium, potassium, barium, calcium salt, and the like, for use as the dosage form. When a basic group is present, such as amino or a basic heteroaryl radical, such as pyridyl, an acidic salt, such as hydrochloride, hydrobromide, phosphate, sulfate, trifluoroacetate, trichloroacetate, acetate, oxalate, maleate, pyruvate, malonate, succinate, citrate, tartrate, fumarate, mandelate, benzoate, cinnamate, methanesulfonate, ethanesulfonate, picrate and the like, and include acids related to the pharmaceutically-acceptable salts listed in the Journal of Pharmaceutical Science, vol. 66, (1977) p. 1-19.

Unless otherwise stated, structures depicted herein are also meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

The ability of a compound of Formula (I) or pharmaceutically acceptable salts thereof to inhibit the interaction of RAGE with its physiological ligands was established with a compound of Formula (I) or a pharmaceutically acceptable salt thereof using assay(s) similar to those described in the Examples section below. Further, the intermediates used to prepare a compound of Formula (I) or a pharmaceutically acceptable salt thereof may also be useful to inhibit the interaction of RAGE with its physiological ligands.

The invention further provides pharmaceutical compositions comprising a compound of Formula (I) or a pharmaceutically acceptable salt thereof and a pharmaceutically acceptable carrier. The term "pharmaceutical composition" is used herein to denote a composition that may be administered to a mammalian host, e.g., orally, topically, parenterally, by inhalation spray, or rectally, in unit dosage formulations containing conventional non-toxic carriers, diluents, adjuvants, vehicles and the like. The term "parenteral" as used herein, includes subcutaneous injections, intravenous, intramuscular, intracisternal injection, or by infusion techniques.

The pharmaceutical compositions containing a compound of the invention may be in a form suitable for oral use, for example, as tablets, troches, lozenges, aqueous, or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid;

binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions or suspensions, lotions, eye ointments and eye or ear drops, impregnated dressings and aerosols etc., containing the compounds of the invention are contemplated. These topical formulations may contain appropriate conventional additives such as preservatives, solvents to assist drug penetration and emollients in ointments and creams. The formulations may also contain compatible conventional carriers, such as cream or ointment bases and ethanol or oleyl alcohol for lotions. Such carriers may be present as from about 0.1% up to about 99% of the formulation. More usually they will form up to about 80% of the formulation. For the purpose of this application, topical applications shall include mouth washes and gargles.

The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

For administration by inhalation the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

Compounds that antagonize the interaction of RAGE with its physiological ligands are potentially useful in treating diseases or conditions that may be responsive to the inhibition of the RAGE receptor.

The present invention provides a method of treatment comprising: administering to a subject a compound of Formula (I) or a pharmaceutically acceptable salt thereof. In an embodiment of this embodiment, the present invention provides a method for the inhibition of the interaction of RAGE with its physiological ligands. In another embodiment of this embodiment, the present invention provides a method for treating a disease state selected from the group consisting of acute and chronic inflammation including skin inflammation such as psoriasis, atopic dermatitis, inflammation associated with organ, tissue, or cell transplantation, and lung inflammation including, asthma and chronic osbtructive pulmonary disease, sepsis, diabetes, diabetes related complications, renal failure, hyperlipidemic atherosclerosis associated with diabetes, neuronal cytotoxicity, restenosis, Down's syndrome, dementia associated with head trauma, amyotrophic lateral sclerosis, multiple sclerosis, amyloidosis, an autoimmune disease, wound healing, periodontal disease, neuropathy, neuronal degeneration, vascular permeability, nephropathy, atherosclerosis, retinopathy, Alzheimer's disease, erectile dysfunction, tumor invasion and/or metastasis, and osteoporosis which comprises administering to a subject a compound of a compound of Formula (I) or a pharmaceutically acceptable salt thereof.

In another embodiment, the subject is suffering from diabetes. In another embodiment, the subject is suffering type 1 diabetes (T1D). In another embodiment, the subject is suffering from type 2 diabetes (T2D).

As noted above, the compounds of the present invention may be useful in the treatment of the complications of diabetes. It has been shown that nonenzymatic glycoxidation of macromolecules ultimately resulting in the formation of advanced glycation endproducts (AGEs) is enhanced at sites of inflammation, in renal failure, in the presence of hyperglycemia and other conditions associated with systemic or local oxidant stress (Dyer, D., et al., J. Clin. Invest., 91:2463-2469 (1993); Reddy, S., et al., Biochem., 34:10872-10878 (1995); Dyer, D., et al., J. Biol. Chem., 266:11654-11660 (1991); Degenhardt, T., et al., Cell Mol. Biol., 44:1139-1145 (1998)). Accumulation of AGEs in the vasculature can occur focally, as in the joint amyloid composed of AGE-ß2-microglobulin found in patients with dialysis-related amyloidosis (Miyata, T., et al., J. Clin. Invest., 92:1243-1252 (1993); Miyata, T., et al., J. Clin. Invest., 98:1088-1094 (1996)), or generally, as exemplified by the vasculature and tissues of patients with diabetes (Schmidt, A-M., et al., Nature Med., 1:1002-1004 (1995)). The progressive accumulation of AGEs over time in patients with diabetes suggests that endogenous clearance mechanisms are not able to function effectively at sites of AGE deposition. Such accumulated AGEs have the capacity to alter cellular properties by a number of mechanisms. Although RAGE is expressed at low levels in normal tissues and vasculature, in an environment where the receptor's ligands accumulate, it has been shown that RAGE becomes upregulated (Li, J. et al., J. Biol. Chem., 272:16498-16506 (1997); Li, J., et al., J. Biol. Chem., 273:30870-30878 (1998); Tanaka, N., et al., J. Biol. Chem., 275:25781-25790(2000)). RAGE expression is increased in endothelium, smooth muscle cells and infiltrating mononuclear phagocytes in diabetic vasculature. Also, studies in cell culture have demonstrated that AGE-RAGE interaction caused changes in cellular properties important in vascular homeostasis.

Also as noted above, the compounds of the present invention may be useful in treating amyloidoses and/or Alzheimer's Disease. RAGE appears to be a cell surface receptor which binds ß-sheet fibrillar material regardless of the composition of the subunits (amyloid-ß peptide, Aß, amylin, serum amyloid A, prion-derived peptide) (Yan, S.-D., et al., Nature, 382:685-691 (1996); Yan, S-D., et al., Nat. Med., 6:643-651 (2000)). Deposition of amyloid has been shown to result in enhanced expression of RAGE. For example, in the brains of patients with Alzheimer's disease (AD), RAGE expression increases in neurons and glia (Yan, S.-D., et al., Nature 382:685-691 (1996)). The consequences of Aß interaction with RAGE appear to be quite different on neurons versus microglia. Whereas microglia become activated as a consequence of Aß-RAGE interaction, as reflected by increased motility and expression of cytokines, early RAGE-mediated neuronal activation is superceded by cytotoxicity at later times. Further evidence of a role for RAGE in cellular interactions of Aß concerns inhibition of Aß-induced cerebral vasoconstriction and transfer of the peptide across the blood-brain barrier to brain parenchyma when the receptor was blocked (Kumar, S., et al., Neurosci. Program, p 141 (2000)). Inhibition of RAGE-amyloid interaction has been shown to decrease expression of cellular RAGE and cell stress markers (as well as NF-kB activation), and diminish amyloid deposition (Yan, S-D., et al., Nat. Med., 6:643-651 (2000)) suggesting a role for RAGE-amyloid interaction in both perturbation of cellular properties in an environment enriched for amyloid (even at early stages) as well as in amyloid accumulation.

In other studies using a mouse model of Alzheimer's Disease, it has been shown that RAGE antagonists may reverse the formation of plaques and the loss of cognition. In U.S. Patent Publication No. US 2005/0026811, small molecule RAGE antagonists were used to inhibit the progression of Aβ deposition and reduced the volume of pre-existing plaques in Alzheimer's Disease mice (US 2005/0026811 at ¶¶581-590).

Also, it had been shown in both cellular assays and in animal studies that RAGE mediates the transcytosis of circulating Aβ across the blood-brain barrier (BBB). Such increased transcytosis of Aβ results in neuronal oxidant stress and sustained reductions in cerebral blood flow. The effects of RAGE can be inhibited by a RAGE modulator (e.g., anti-RAGE antibody or sRAGE) (see e.g., Mackic et al., J. Clin. Invest., 102:734-743 (1998); see also Kumar et al., Neurosci., Program, p 141 (2000)). These finding were confirmed by additional studies (see e.g., U.S. Pat. No. 6,825,164 at col. 17, line 48 to col. 18, line 43; Deane et al., Nature Medicine, 9:907-913 (2003)). Reduced cerebral perfusion can promote ischemic lesions which can act synergistically with Aβ to exacerbate dementia. Also, insufficient cerebral blood flow may alter Aβ trafficking across the blood brain barrier thereby reducing Aβ clearance and promoting accumulation of Aβ in brain (see Girouard and Iadecola, J. Appl. Physiol., 100, 328-335 (2006) at page 332). Thus, the increase in cerebral blood flow promoted by RAGE antagonists may reduce the symptoms or delay onset of development of Alzheimer's Disease, or both. For example, RAGE antagonists may delay or slow loss of cognitive performance, or may improve cognitive performance of a subject suffering from dementia of Alzheimer's type, or both.

As noted above, the compound of the present invention may be useful in treating inflammation. For example, S100/calgranulins have been shown to comprise a family of closely related calcium-binding polypeptides characterized by two EF-hand regions linked by a connecting peptide (Schafer, B. et al., TIBS, 21:134-140 (1996); Zimmer, D., et al., Brain Res. Bull., 37:417-429 (1995); Rammes, A., et al., J. Biol. Chem., 272:9496-9502 (1997); Lugering, N., et al., Eur. J. Clin. Invest., 25:659-664 (1995)). Although they lack signal peptides, it has long been known that S100/calgranulins gain access to the extracellular space, especially at sites of chronic immune/inflammatory responses, as in cystic fibrosis and rheumatoid arthritis. RAGE is a receptor for many members of the S100/calgranulin family, mediating their proinflammatory effects on cells such as lymphocytes and mononuclear phagocytes. Also, studies on delayed-type hypersensitivity response, colitis in IL-10 null mice, collagen-induced arthritis, and experimental autoimmune encephalitis models suggest that RAGE-ligand interaction (presumably with S100/calgranulins) has a proximal role in the inflammatory cascade as implicated in the inflammatory diseases such as but not limited to rheumatoid arthritis and multiple sclerosis.

RAGE is also implicated in inflammatory diseases of the skin such as but not limited to atopic dermatitis, eczema, and psoriasis. Psoriasis in particular is characterized by inflamed itchy lesions. Psoriasis may be accompanied by arthropathic symptoms that are similar to those in seen in rheumatoid arthritis. There is considerable evidence that psoriasis is a polygenic autoimmune disorder. Psoriatic lesions are rich in cytokines, in particular IL-1 and IL-8, both potent proinflammatory mediators. IL-8 in particular is a chemotactic factor for neutrophils; neutrophils are also known to synthesize and secrete S100 proteins, one of the ligands for RAGE which is implicated in propagation of the immune and inflammatory response. Psoriasin, (S100A7) a new member of the 5100 gene family, is a secreted protein isolated from psoriatic skin. Semprini et al. (Hum. Genet. 2002 October, 111(4-5), 310-3) have shown a linkage of psoriasis genetic susceptibility to distinct overexpression of S100 proteins in skin. Therefore, a modulator of RAGE would be expected to regulate the immune response in psoriasis.

As noted above, the compounds of the present invention may be useful in treating tumor and tumor metastasis. For example, amphoterin is a high mobility group I nonhistone chromosomal DNA binding protein (Rauvala, H., et al., J. Biol. Chem., 262:16625-16635 (1987); Parkikinen, J., et al., J. Biol. Chem. 268:19726-19738 (1993)) which has been shown to interact with RAGE. It has been shown that amphoterin promotes neurite outgrowth, as well as serving as a surface for assembly of protease complexes in the fibrinolytic system (also known to contribute to cell mobility). In addition, a local tumor growth inhibitory effect of blocking RAGE has been observed in a primary tumor model (C6 glioma), the Lewis lung metastasis model (Taguchi, A., et al., Nature 405:354-360 (2000)), and spontaneously arising papillomas in mice expressing the v-Ha-ras transgene (Leder, A., et al., Proc. Natl. Acad. Sci., 87:9178-9182 (1990)).

Airway inflammation is important in the pathogenesis of asthma. Such inflammation may give rise to significant exacerbations and increases in asthma severity, as well as to be a major factor in a decline in asthmatic status. In severe exacerbations of asthma there is an intense, mechanistically heterogeneous inflammatory response involving neutrophil and eosinophil accumulation and activation. Neutrophils are a significant source of S100 proteins, key ligands for RAGE implicated in the propagation of the immune response and inflammation. Therefore, modulators of RAGE would be expected to possess therapeutic value in the treatment of asthma. Further, the propagation step in the immune response in the lung driven by S100-RAGE interaction would be expected to lead to the activation and/or recruitment of inflammatory cells, such as neutrophils, which in chronic obstructive pulmonary diseases such as emphysema, are significant sources of damaging proteases. Therefore, a RAGE modulator would be expected possess potential in the treatment of chronic obstructive pulmonary diseases.

As used herein, the phrase "therapeutically effective amount" shall mean that amount of a drug or pharmaceutical agent that will elicit the therapeutic response of a subject that is being sought.

In these methods, factors which may influence what constitutes a therapeutically effective amount include, but are not limited to, the size and weight of the subject, the biodegradability of the therapeutic agent, the activity of the therapeutic agent, the size of the effected area, as well as its bioavailability. The phrase includes amounts which, as compared to a corresponding subject who has not received such amount, results in improved treatment, healing, or amelioration of a side effect, or a decrease in the rate of advancement of a disease or disorder.

In another embodiment, the present invention provides a method for treating restenosis comprising: administering to a subject a therapeutically effective amount of a compound of Formula (I) or a pharmaceutically acceptable salt thereof.

In an embodiment, the present invention provides a method for treating acute or chronic inflammation comprising: administering to a subject a therapeutically effective amount of a compound of Formula (I) or a pharmaceutically acceptable salt thereof.

In an embodiment, the present invention provides a method for treating dementia associated with head trauma comprising: administering to a subject a therapeutically effective amount of a compound of Formula (I) or a pharmaceutically acceptable salt thereof. In an embodiment, the cognitive performance of the subject is improved. In another embodiment, the cognitive performance of the subject is maintained. In another embodiment, the rate of loss of cognitive performance of the subject is slowed.

In an embodiment, the present invention provides a method for treating Alzheimer's Disease comprising: administering to a subject a therapeutically effective amount of a compound of Formula (I) or a pharmaceutically acceptable salt thereof. With respect to Alzheimer's Disease, the present invention is believed useful in alteration the course of the underlying dementing process. Alzheimer's Disease may be diagnosed by NINCDS and DSM criteria, Mini-Mental State Examination, and Clinical Dementia Rating within particular limits. One embodiment of the present invention includes improving cognitive performance comprising administering a compound of Formula (I) or a pharmaceutically acceptable salt thereof. Cognitive performance may be assessed with the cognitive subscale of the Alzheimer's Disease Assessment Scale (ADAS-cog), as is known in the art, which scores cognitive function on a 0 to 70 scale, with higher scores indicating greater cognitive impairment. Thus, a reduction in score demonstrates cognitive improvement. One embodiment of the present invention includes administering to a subject a compound of Formula (I) or a pharmaceutically acceptable salt thereof to reduce an ADAS-cog score of a subject in need of such reduction. Such a subject may be a human be suffering from dementia of Alzheimer's type, mild to moderate Alzheimer's Diseases, or severe Alzheimer's Disease.

In addition, the progression of Alzheimer's Disease may also be assessed in a human through examination of four areas of function: General, Cognitive, Behavioral, and Activities of Daily Living. Such an assessment may be performed using a Clinician's Interview Based Impression of Change (CIBIC or CIBIC plus). One embodiment of the present invention includes improvement in subject's function comprising administering a compound of Formula (I) or a pharmaceutically acceptable salt thereof. In one embodiment, the subject's function is one or more of general, cognitive, behavioral, and activities of daily living.

In another embodiment, the present invention provides a method of delaying onset of type 1 or type 2 diabetes comprising administering to the subject a therapeutically effective amount of a compound of Formula (I) or a pharmaceutically acceptable salt thereof. The method may comprise adminisitering a compound of Formula (I) or a pharmaceutically acceptable salt thereof prior to onset of type 1 diabetes or prior to onset of type 2 diabetes.

In another embodiment, the present invention provides a method of delaying onset of type 1 or type 2 diabetes comprising administering to the subject a therapeutically effective amount of a compound of Formula (I) or a pharmaceutically acceptable salt thereof so as to preserve pancreatic function. Pancreatic function may include preservation of ability of beta-cells to secret insulin. The method may comprise adminisitering a compound of Formula (I) or a pharmaceutically acceptable salt thereof prior to onset of type 1 diabetes or prior to onset of type 2 diabetes.

In an embodiment, the present invention provides a method for improving wound healing in a diabetic subject comprising: administering to the subject a therapeutically effective amount of a compound of Formula (I) or a pharmaceutically acceptable salt thereof, so as to improve the rate of wound healing in the subject relative to an untreated wound.

In an embodiment, the present invention provides a method for treating in a subject inflammation associated with transplantation of an organ, a tissue or a plurality of cells from a first site to a second site comprising: administering to the subject a therapeutically effective amount of a compound of Formula (I) or a pharmaceutically acceptable salt thereof, so as to reduce inflammation in the subject. In an embodiment, the first and second sites are in different subjects. In another embodiment, the first and second sites are in the same subject. In another embodiment, the transplanted organ, cells or tissue comprise a cell or tissue of a pancreas, skin, liver, kidney, heart, bone marrow, blood, bone, muscle, artery, vein, cartilage, thyroid, nervous system, or stem cells.

In an embodiment, the present invention provides a method for reducing renal damage in a subject suffering from T1D, comprising: administering to the subject a therapeutically effective amount of a compound of Formula (I) or a pharmaceutically acceptable salt thereof, so as to reduce renal damage in the subject.

In another embodiment, at least one compound of Formula (I) or a pharmaceutically acceptable salt thereof is utilized, either alone or in combination with one or more known therapeutic agents As used herein, the phrase "a subject" refers to mammalian subjects, and in one group of embodiments, humans, who either suffer from one or more of the aforesaid diseases or disease states or are at risk for such.

In a further embodiment of the present invention, the RAGE inhibitors of the invention may be used in adjuvant therapeutic or combination therapeutic treatments with other known therapeutic agents.

The following is a non-exhaustive listing of adjuvants and additional therapeutic agents which may be utilized in combination with the RAGE inhibitors of the present invention:
Pharmacologic classifications of anticancer agents:
1. Alkylating agents: Cyclophosphamide, nitrosoureas, carboplatin, cisplatin, procarbazine
2. Antibiotics: Bleomycin, Daunorubicin, Doxorubicin
3. Antimetabolites: Methotrexate, Cytarabine, Fluorouracil
4. Plant alkaloids: Vinblastine, Vincristine, Etoposide, Paclitaxel,
5. Hormones: Tamoxifen, Octreotide acetate, Finasteride, Flutamide
6. Biologic response modifiers: Interferons, Interleukins, Anti-tumor antibodies Pharmacologic classifications of treatment for Rheumatoid Arthritis (Inflammation)
1. Analgesics: Aspirin
2. NSAIDs (Nonsteroidal anti-inflammatory drugs): Ibuprofen, Naproxen, Diclofenac
3. DMARDs (Disease-Modifying Antirheumatic drugs): Methotrexate, gold preparations, hydroxychloroquine, sulfasalazine
4. Biologic Response Modifiers, DMARDs: Etanercept, Infliximab Glucocorticoids Pharmacologic classifications of treatment for Diabetes Mellitus
1. Sulfonylureas: Tolbutamide, Tolazamide, Glyburide, Glipizide
2. Biguanides: Metformin
3. Miscellaneous oral agents: Acarbose, Troglitazone
4. Insulin Pharmacologic classifications of treatment for Alzheimer's Disease
1. Cholinesterase Inhibitor: Tacrine, Donepezil
2. Antipsychotics: Haloperidol, Thioridazine
3. Antidepressants: Desipramine, Fluoxetine, Trazodone, Paroxetine
4. Anticonvulsants: Carbamazepine, Valproic acid
5. NMDA Receptor Antagonists: Memantine In a further embodiment, the present invention provides a method of treating a RAGE mediated disease, the method comprising administering to a subject a therapeutically effective amount of a compound of Formula (I) or a pharmaceutically acceptable salt thereof in combination with a therapeutic agent selected from the group consisting of alkylating agents, antimetabolites, plant alkaloids, antibiotics, hormones, biologic response modifiers, analgesics, NSAIDs, DMARDs, glucocorticoids, sulfonylureas, biguanides, insulin, cholinesterase inhibitors, antipsychotics, antidepressants, anticonvulsants and NMDA receptor antagonists.

In a further embodiment, the present invention provides the pharmaceutical composition of the invention as described above, further comprising one or more therapeutic agents selected from the group consisting of alkylating agents, antimetabolites, plant alkaloids, antibiotics, hormones, biologic response modifiers, analgesics, NSAIDs, DMARDs, glucocorticoids, sulfonylureas, biguanides, insulin, cholinesterase inhibitors, antipsychotics, antidepressants, anticonvulsants and NMDA receptor antagonists.

Such other therapeutic agents may be administered by a like route or different route that the compound of Formula (I) or a pharmaceutically acceptable salt thereof. Where a compound of Formula (I) or a pharmaceutically acceptable salt thereof is used in combination with another therapeutic agent, the composition may contain the compound of Formula (I) or a pharmaceutically acceptable salt thereof in combination with the other therapeutic agent(s). Alternatively, where separate dosage formulations are used, the compound of Formula (I) or a pharmaceutically acceptable salt thereof and one or more additional therapeutic agents may be administered at essentially the same time (e.g., concurrently) or at separately staggered times (e.g., sequentially).

Generally speaking, a compound of Formula (I) or a pharmaceutically acceptable salt thereof may be administered at a dosage level of from about 0.003 to 500 mg/kg of the body weight of the subject being treated. In an embodiment, a compound of Formula (I) or a pharmaceutically acceptable salt thereof may be administered at a dosage range between about 0.003 and 200 mg/kg of body weight per day. In an embodiment, a compound of Formula (I) or a pharmaceutically acceptable salt thereof may be administered at a dosage range between about 0.1 to 100 mg/kg of body weight per day, or between about 0.05 to 2 mg/kg of body weight per day. The amount of active ingredient that may be combined with the carrier materials to produce a single dosage may vary depending upon the host treated and the particular mode of administration. For example, a formulation intended for oral administration to humans may contain 1 mg to 2 grams of a compound of Formula (I) or a pharmaceutically acceptable salt thereof with an appropriate and convenient amount of carrier material which may vary from about 5 to 95 percent of the total composition. A dosage form intended for topical administration to the skin may be prepared at 0.1% to 99% compound to topical excipient ratio. A dosage form intended for inhaled administration of 0.01 to 200 mg of compound in a suitable carrier to deliver an inhaled dosage of compound. Dosage unit forms of systemically delivered compound may generally contain between from about 5 mg to about 500 mg of active ingredient or from about 1 mg to about 500 mg of active ingredient. This dosage may be individualized by the clinician based on the specific clinical condition of the subject being treated. Thus, it will be understood that the specific dosage level for any particular subject will depend upon a variety of factors including the activity of the specific compound employed, the age, body weight, general health, sex, diet, time of administration, route of administration, rate of excretion, drug combination, size of effected area and the severity of the particular disease undergoing therapy.

The compounds of this invention may be made by a variety of methods well known to those of ordinary skill in the art including the methods are set out below in the Examples.

In another embodiment, the present invention also provides a method for the synthesis of compounds useful as intermediates in the preparation of compounds of the present invention along with methods for their preparation.

While the invention has been described and illustrated with reference to certain embodiments, the invention also provides other embodiments that may use any combination or subsets of elements as described in any of the above embodiments.

Examples

LC-MS data are obtained using gradient elution on a parallel MUX™ system, running four Waters 1525 binary HPLC pumps, equipped with a Mux-UV 2488 multichannel UV-Vis detector (recording at 215 and 254 nM) and a Leap Technologies HTS PAL Auto sampler using a Sepax GP-C18, 4.6×50 mm; 5 micron particle-size column. In general, a three minute gradient is run from 25% B (97.5% acetonitrile, 2.5% water, 0.05% TFA) and 75% A (97.5% water, 2.5% acetonitrile, 0.05% TFA) to 100% B. The system is interfaced with a Waters Micromass ZQ mass spectrometer using electrospray ionization. MassLynx software is employed. All MS data were obtained in the positive mode unless otherwise noted. The reported m/z data are generally accurate within about ±1 for the M+ ion.

$^1$H NMR data were obtained on a Varian Mercury 400 MHz spectrometer and chemical shifts were referenced using either the residual solvent proton signal (e.g., residual $CHCl_3$ in $CDCl_3$) or the TMS signal as an internal reference. Microwave heating procedures were used in some experiments and, in these cases, a DISCOVER microwave synthesis system (CEM, Matthews, N.C., USA) was used which included the use of pressurized glass reaction vessels at elevated temperatures.

Abbreviations

Below are definitions of some common abbreviations that are used in the specification. The specification may also employ other abbreviations whose meanings are well known in the relevant art.

d=day
DCM=dichloromethane
DMAP=4-(dimethylamino)-pyridine
g=gram
h=hour
Hz=hertz
L=liter
LC=liquid chromatography
LCMS, LC-MS=liquid chromatography-mass spectroscopy
M=molar
m/z=mass to charge ratio
mg=milligram
min=minute
mL=milliliter
mM=millimolar
mmol=millimole
mol=mole
MS=mass spectrometry
N=normal
NMP=N-methylpyrrolidinone
NMR=nuclear magnetic resonance spectroscopy
ppm=parts per million
rt or RT=room temperature
TFA=trifluoroacetic acid
THF=tetrahydrofuran General Procedures The following procedures provide instructions for carrying out syntheses that are useful for making the compound of Formula (I) or a pharmaceutically acceptable salt thereof. The procedures are intended to be general in nature. Substitution of certain solvents, adjustment of the scale, and the like are possible, according to the knowledge of the skilled artisan. When incorporated into the synthesis of the compound of Formula (I) or intermediates, the general procedures may have been adjusted to a smaller or larger scale.

Procedure A: Reduction of an Amide Bond

A solution of an amide (1 mmol) in THF (1 mL) and borane-THF complex (1.44 mmol) were taken in microwave reaction vessel. The reaction was heated to 140° C. at 300 watts with no continuous cooling for 12 min. After cooling, the reaction was quenched by addition to 10 mL methanol and was stirred for 30 min. The solvent was evaporated under reduced pressure and the crude product was stirred with N, N-dimethylethylamine (10 mmol) for 1 h. After evaporation of the amine under reduced pressure, the crude product was taken up in ethyl acetate (20 mL) and washed with water (2×5 mL), brine (2×5 mL), dried over $Na_2SO_4$, and concentrated under reduced pressure to afford the product. The crude product was purified by silica gel flash column chromatography.

Procedure B: Synthesis of a Sulfonamide

To a stirred solution of an amine (1 mmol) in DCM (1 mL) was added triethylamine (3 mmol) followed by a sulfonyl chloride (1.2 to 1.5 mmol) under $N_2$ atmosphere. To this was added a catalytic amount of DMAP (0.1 mmol). The resultant reaction was stirred for 2 h at rt. The reaction mixture was diluted with DCM (10 mL), washed with water (2×5 mL), dried over $Na_2SO_4$, and concentrated under reduced pressure. The crude sulfonamide was purified by silica gel flash column chromatography.

Procedure C: Removal of a BOC Group

To a stirred solution of carbamate (1 mmol) in DCM (1 mL) was added 4 N HCl in dioxane (5 mL). The reaction was stirred at rt for 30 min. Solvents were removed under reduced pressure. The residue was triturated with ethyl ether and the precipitated solid was filtered and dried under vacuum.

Procedure D: Reductive Amination of an Aldehyde or a Ketone

A mixture of an aldehyde or ketone (1 mmol) and amine (1.5 mmol) in DCM (5 ml) was stirred for 15 min at rt. To this was added $NaBH(OAc)_3$ (5 mmol) in one lot and the reaction mixture was stirred until all the carbonyl derivative was consumed as judged by LCMS. The reaction was quenched with saturated $NaHCO_3$ solution (10 ml) and stirred for 30 min. The organic layer was separated and the aqueous layer was extracted with DCM (5 mL). The combined organic layer was washed with brine (5 mL), dried over $Na_2SO_4$ and concentrated under reduced pressure. The crude amine was purified by silica gel flash column chromatography.

Procedure E: Synthesis of a 1-N-substituted 3,5-dimethylpyrazole

A mixture of 2.4-pentanedione (83 mmol) and an alkyl or arylhydrazine hydrochloride (66.4 mmol) was taken into ethanol (20 mL) in a 80 ml microwave reaction vessel. To this solution was added p-toluenesulfonic acid monohydrate (3.32 mmol) and the reaction was heated in the microwave reactor at 150° C. for 12 min at 300 watts with no continuous cooling. The solvent was evaporated and the residue was purified by silica gel flash column chromatography.

Procedure F: Chlorosulfonation of a 1-N-substituted 3,5-dimethylpyrazole

To a stirred solution of N-substituted-3,5-dimethyl-1H-pyrazole (100 mmol) in DCM (20 mL) at 0-5° C. (ice bath) was added chlorosulfonic acid (900 mmol) dropwise under $N_2$ atmosphere. The cold bath was removed. The reaction mixture was allowed to come to rt, then was heated to 90° C. for 2 h. After cooling to rt, the reaction was carefully poured onto 300 g of ice (CAUTION: chlorosulfonic acid reacts vigorously with water). The mixture was extracted with ethyl acetate or DCM (2×200 mL). The combined organic layers were washed with water (50 mL), dried over $Na_2SO_4$, and concentrated under reduced pressure. The residue was purified by silica gel flash column chromatography.

Preparation of Intermediates

In the making of the compound of Formula (I) or salts thereof, it may be useful to synthesize certain intermediate compounds. The synthetic procedures for these intermediates are provided exclusively for purposes of illustration. As the skilled artisan will recognize, the procedures below may not be the exclusive means by which such intermediates are made.

Intermediate 1:
1-Cyclohexyl-3,5-dimethyl-1H-pyrazole-4-sulfonyl chloride

Step 1: 1-Cyclohexyl-3,5-dimethyl-1H-pyrazole was prepared from cyclohexylhydrazine hydrochloride and 2,4-pentanedione using Procedure E. The product was purified using 12% ethyl acetate in hexanes on silica gel.

Step 2: 1-Cyclohexyl-3,5-dimethyl-1H-pyrazole-4-sulfonyl chloride (Intermediate 1) was prepared from 1-cyclohexyl-3,5-dimethyl-1H-pyrazole using Procedure F. The product was purified using 10% ethyl acetate in hexanes on silica gel.

Intermediate 2: 4-Formyl-N-isobutyl-N-(4-phenyl-piperidin-4-ylmethyl)-benzenesulfonamide hydrochloride Step 1: 4-Isobutylcarbamoyl-4-phenyl-piperidine-1-carboxylic acid tert-butyl ester was prepared from 1-tert-butoxycarbonyl-4-phenyl-piperidine-4-carboxylic acid and isobutyl amine according to Procedure E. LCMS: m/z 362 [M+2]. $^1$H NMR (400 MHz, $CDCl_3$): δ 7.37-7.41 (m, 4H), 7.27-7.36 (m, 1H), 5.20 (br t, 1H), 3.50 (m, 4H), 2.96 (t, 2H), 2.34 (m, 2H), 2.03 (br d, 2H), 1.58-1.71 (m, 1H), 1.44 (s, 9H), 0.72 (d, 6H) ppm.

Step 2: 4-(Isobutylamino-methyl)-4-phenyl-piperidine-1-carboxylic acid tert-butyl ester was prepared from 4-isobutylcarbamoyl-4-phenyl-piperidine-1-carboxylic acid tert-butyl ester following Procedure A. LCMS: m/z 348 [M+2]. $^1$H NMR (400 MHz, $CDCl_3$): δ 7.32-7.38 (m, 4H), 7.20-7.24 (m, 1H), 3.64 (br d, 2H), 3.10-3.17 (m, 2H), 2.65 (s, 2H), 2.05-2.23 (m, 4H), 1.78-1.84 (m, 2H), 1.55-1.62 (m, 1H), 0.1.44 (s, 9H), 0.72 (d, 6H) (NH hydrogen not visible) ppm.

Step 3: 4-{[(4-Formyl-benzenesulfonyl)-isobutyl-amino]-methyl}-4-phenyl-piperidine-1-carboxylic acid tert-butyl ester was prepared from 4-(isobutylamino-methyl)-4-phenyl-piperidine-1-carboxylic acid tert-butyl ester and 4-formylbenzenesulfonyl chloride according to Procedure B. LCMS: m/z 516 [M+2]. $^1$H NMR (400 MHz, $CDCl_3$): δ 10.08 (s, 1H), 7.96-7.99 (m, 2H), 7.90-7.92 (m, 2H), 7.33-7.38 (m, 4H), 7.23-7.25 (m, 1H), 3.91 (br d, 2H), 3.44 (br d, 2H), 2.76-2.98 (m, 2H), 2.20-2.42 (m, 4H), 1.83 (br s, 2H), 0.1.44 (s, 9H), 1.31-1.38 (m, 1H), 0.29 (d, 6H) ppm.

Step 4: 4-Formyl-N-isobutyl-N-(4-phenyl-piperidin-4-ylmethyl)-benzenesulfonamide hydrochloride (Intermediate 2) was prepared from 4-{[(4-formyl-benzenesulfonyl)-isobutyl-amino]-methyl}-4-phenyl-piperidine-1-carboxylic acid tert-butyl ester according to Procedure C. LCMS: m/z 416 [M+2]. $^1$H NMR (400 MHz, $CDCl_3$): δ 10.08 (s, 1H), 9.49 (br d, 2H), 7.94-8.00 (m, 4H), 7.36-7.40 (m, 4H), 7.28-7.32 (m, 1H), 3.71 (s, 2H), 3.45-3.52 (m, 1H), 2.92-2.97 (m, 2H), 2.55-2.58 (m, 2H), 2.26-2.36 (m, 4H), 2.06 (br s, 1H), 1.25-1.31 (m, 1H), 0.23 (d, 6H) ppm.

Synthesis of N-[1-(1-Cyclohexyl-3,5-dimethyl-1H-pyrazole-4-sulfonyl)-4-phenyl-piperidin-4-ylmethyl]-N-isobutyl-4-{[(piperidin-4-ylmethyl)-amino]-methyl}-benzenesulfonamide dihydrochloride

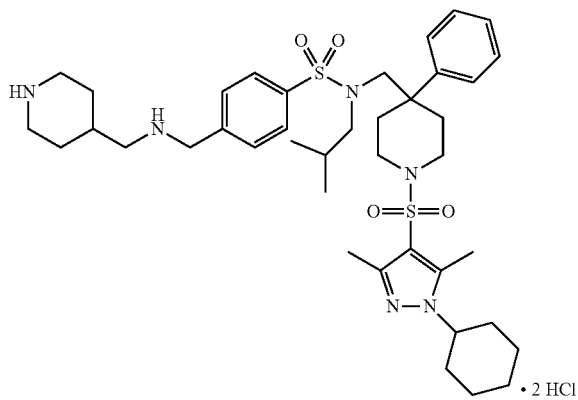 [SMILES: Cc1nn(C2CCCCC2)c(C)c1S(=O)(=O)N1CCC(CN(CC(C)C)S(=O)(=O)c2ccc(CNCC3CCNCC3)cc2)(c2ccccc2)CC1]

Step 1: N-[1-(1-Cyclohexyl-3,5-dimethyl-1H-pyrazole-4-sulfonyl)-4-phenyl-piperidin-4-ylmethyl]-4-formyl-N-isobutyl-benzenesulfonamide may be prepared using 4-formyl-N-isobutyl-N-(4-phenyl-piperidin-4-ylmethyl)-benzenesulfonamide hydrochloride (Intermediate 2) and 1-cyclohexyl-3,5-dimethyl-1H-pyrazole-4-sulfonyl chloride (Intermediate 1) using Procedure B. The product may be purified using 30% ethyl acetate in hexanes on silica gel.

Step 2: 4-[(4-{[1-(1-Cyclohexyl-3,5-dimethyl-1H-pyrazole-4-sulfonyl)-4-phenyl-piperidin-4-ylmethyl]-isobutyl-sulfamoyl}-benzylamino)-methyl]-piperidine-1-carboxylic acid tert-butyl ester may be prepared from N-[1-(1-cyclohexyl-3,5-dimethyl-1H-pyrazole-4-sulfonyl)-4-phenyl-piperidin-4-ylmethyl]-4-formyl-N-isobutyl-benzenesulfonamide and 4-aminomethylpiperidine-1-carboxylic acid tert-butyl ester using Procedure D. The product may be purified using 2% 2 N $NH_3$/MeOH in DCM on silica gel.

Step 3: The title compound (N-[1-(1-cyclohexyl-3,5-dimethyl-1H-pyrazole-4-sulfonyl)-4-phenyl-piperidin-4-ylmethyl]-N-isobutyl-4-{[(piperidin-4-ylmethyl)-amino]-methyl}-benzenesulfonamide dihydrochloride) may be prepared from 4-[(4-{[1-(1-cyclohexyl-3,5-dimethyl-1H-pyrazole-4-sulfonyl)-4-phenyl-piperidin-4-ylmethyl]-isobutyl-sulfamoyl}-benzylamino)-methyl]-piperidine-1-carboxylic acid tert-butyl ester using Procedure C. The product may be triturated with ethyl ether and dried to give product. LCMS: m/z 754.7 [M+2]. $^1$HNMR (400 MHz, $CD_3OD$): δ 7.78 (d, 2H), 7.66 (d, 2H), 7.37-7.30 (m, 4H), 7.24-7.18 (m, 1H), 4.13 (s, 2H), 4.12-4.04 (m, 1H), 3.44-3.39 (m, 6H), 3.04-2.97 (m, 2H), 2.82 (d, 2H), 2.68-2.61 (m, 2H), 2.44 (s, 3H), 2.34 (br d, 2H), 2.30 (s, 3H), 2.26 (d, 2H), 2.04-1.69 (m, 13H), 1.52-1.40 (m, 4H), 1.31-1.22 (m, 1H), 0.28 (d, 6H) (protons of HCl cation not visible) ppm.

General Binding Assay

The following is one potential method for screening. S100b or β-amyloid (500 ng/100 μL/well) in 100 mM sodium bicarbonate/sodium carbonate buffer (pH 9.8) is loaded onto the wells of a NUNC Maxisorp flat bottom 96-well microtitre plate. The plate is incubated at 4° C. overnight. The wells are aspirated and treated with 50 mM imidazole buffer saline (pH 7.2) (with 5 mM $CaCl_2$/$MgCl_2$) containing 1% bovine serum albumin (BSA) (300 μL/well) for 1 h at RT. The wells are aspirated.

The test compound is dissolved in nanopure water (concentration: 10-100 μM). DMSO may be used as co-solvent. 25 μL of test compound solution in 4% DMSO is added, along with 75 μL sRAGE (6 nM FAC) to each well and samples are incubated for 1 h at 37° C. The wells are washed several times with 155 mM NaCl pH 7.2 buffer saline and are soaked for several seconds between each wash.

Non-Radioactive Detection is Performed by Adding:

10 μL Biotinylated goat F(ab')2 Anti-mouse IgG. (8.0× 10-4 mg/mL, FAC), 5 μL Alk-phos-Streptavidin (3×10-3 mg/mL FAC), 0.42 μL per 5 mL Monoclonal antibody for sRAGE (FAC 6.0×10-3 mg/mL) to 5 mL 50 mM imidazole buffer saline (pH 7.2) containing 0.2% bovine serum albumin and 5 mM $CaCl_2$). The mixture is incubated for 30 minutes at RT.

100 μL of complex is added to each well and incubation is allowed to proceed at rt for 1 h. Wells are washed several times with wash buffer and soaked several seconds between each wash. 100 μL 1 mg/mL (pNPP) in 1 M diethanolamine (pH adjusted to 9.8 with HCl) is added. Color is allowed to develop in the dark for 30 min to 1 h at rt. The reaction is quenched with 10 μL of stop solution (0.5-1.0 N NaOH in 50% ethanol) and the absorbance is measured spectrophotometrically with a microplate reader at 405 nm.

The compound of Formula (I) as a hydrochloride salt was screened in an assay using a procedure similar to those described above, employing S100b or β-amyloid as the RAGE ligand, and was found to possess IC50 concentrations shown below. The IC50 (μM) value in the assay represents the concentration of compound at which 50% signal has been inhibited.

| IC50 (S100b) | IC50 (β-amyloid) |
|---|---|
| 0.22-0.62 μM (0.42 μM average, n = 13) | 0.27-0.60 μM (0.40 μM average, n = 11) |

Functional Assay

Previously the literature has cited that THP-1 cells in response to RAGE ligands secrete TNF alpha (Yeh C-H, et al. Diabetes. Vol. 50, June 2001, pp. 1495-1504). The following assay method may be used to identify compounds of Formula (I) or pharmaceutically acceptable salts thereof which are useful as antagonists of RAGE signaling.

The myeloid cell line, THP-1 (ATTC # TIB-202), is cultured in RPMI-1640 media (ATCC, Cat #30-2001) supplemented with fetal bovine serum to a final concentration of 10% by volume and Penicillin-Streptomycin (Gibco, Cat #0.15140-122). Alternatively, media may be formulated using RPMI 1640 (Bio-Whitaker #12-702F) supplemented with 2 mM L-glutamine (Gibco #12381-018) adjusted to contain 1.5 g/L sodium bicarbonate (Gibco #25080-094), 4.5 g/L glucose, 10 mM HEPES (Cellgro #25-060-L1) and 1.0 mM sodium pyruvate (Gibco #11360-070) and supplemented with 0.05 mM 2-mercaptoethanol, 90% fetal bovine serum, 10% per ATCC instructions. During culture, the culture cells may be maintained at a density between $5 \times 10^4$ and $1 \times 10^6$ viable cells/mL. The cell doubling time is approximately 20 hours and the cells should be passed every 3-4 days.

THP-1 cells may be first harvested by centrifugation and then washed 1 time with RPMI containing Pen Strep without serum. The cells are resuspended to a final concentration of between 5×10⁵ and 1×10⁶ cells/mL in RPMI without serum. The cells are dispensed into a 96-well tissue culture plate (Corning, CSL3599) at 50,000-100,000 cells per well in 100 µL of RPMI. Following plating of cells, compounds are dispensed and serially diluted using DMSO. DMSO and compound concentrations may be adjusted with RPMI to give a final concentration of DMSO no greater than 0.5% in the cell culture. Typically, compounds may be diluted into 50 µL of RPMI prior to addition to culture. Compounds are incubated with the cells for 30 minutes at 37° C. and 5% $CO_2$ to equilibrate the compound in culture. After the 30 minute preincubation, the cells are stimulated with bovine S100b at a final concentration of 100 µg/mL. This material may be prepared by dissolving bovine S100b (Calbiochem, #559290) in RPMI to a final concentration of 0.4 mg/mL. Assays may be run in the presence of a RAGE fusion protein or with sRAGE as a positive control or a human IgG (Sigma #I4506) as a negative control.

The amount of TNF-alpha secreted by the THP-1 cells may be measured 24 hours after the addition of the stimulant proteins to the cell culture using a commercially available ELISA kit (R&D Systems, Minneapolis, Minn. # DY210). All reagents and standards may be prepared as directed by the manufacturer. Then, 100 µL of standards, media controls or media samples may be added to the appropriate ELISA well. The plate may be incubated at room temperature (22-25° C.) for 2 hours. The plate may be then aspirated and washed with 400 µL of wash buffer (PBS+0.1% Tween-20) and repeated three more times for a total of four washes. Next, 100 µL of TNF-alpha detection conjugate may be added to each ELISA well and allowed to incubate at room temperature for one hour. The plate may be then aspirated and washed with 400 µL of wash buffer and repeated three more times for a total of four washes. Next, 100 µL of a preparation of streptavidin conjugated to horseradish peroxidase may be added to each well and allowed to incubate for 20 minutes. The plate may be then aspirated and washed with 400 µL of wash buffer and repeated three more times for a total of four washes. Color development may be initiated by the addition of 100 uL of TMB Substrate Solution (Sigma, T0440-1L) and incubated for 10-20 minutes. The color development may be stopped by addition of 100 µL of 1M phosphoric acid. The plate may be read at 450 nm within 30 minutes. With S100b stimulation, 125-250 pg/mL are seen above background.

The compound of Formula (I) as a hydrochloride salt was screened in an inhibition of S100b mediated TNF release from THP-1 cells assay using a procedure similar to that described above and was found to possess an IC50 concentration of about 0.5 µM.

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth herein may be applicable as a consequence of variations in the responsiveness of the mammal being treated for RAGE-mediated disease(s). Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention.

We claim:

1. A compound, wherein the compound is a compound of Formula (I)

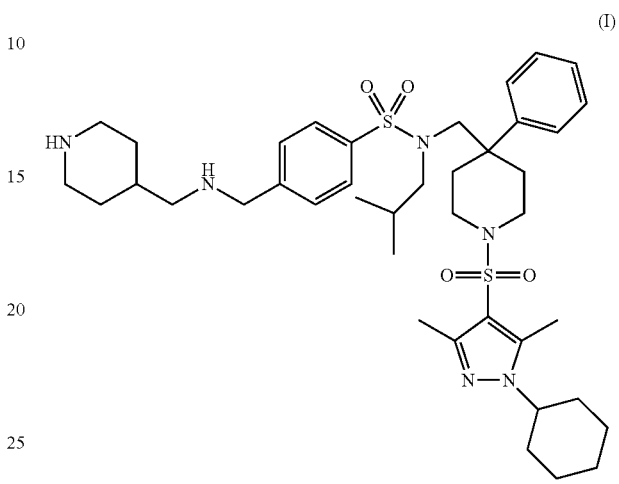

or a pharmaceutically acceptable salt thereof.

2. The compound of claim 1, wherein the compound is the compound of Formula (I).

3. The compound of claim 1, wherein the compound is a pharmaceutically acceptable salt of the compound of Formula (I).

4. The compound of claim 1, wherein the compound is a hydrochloride salt of the compound of Formula (I).

5. A pharmaceutical composition comprising a compound of Formula (I)

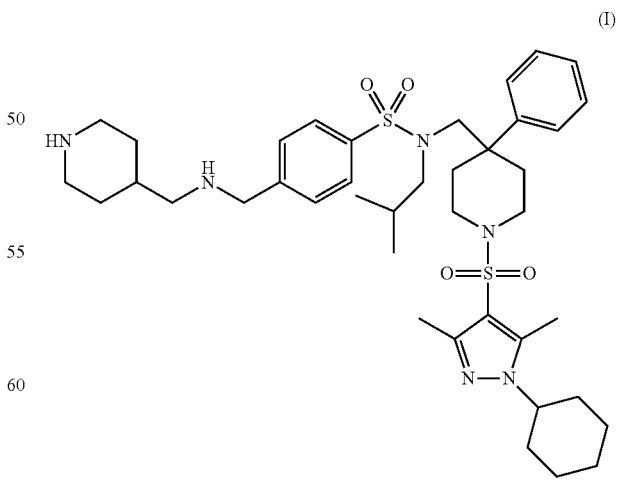

or a pharmaceutically acceptable salt thereof, and a pharmaceutically acceptable carrier.

6. A pharmaceutical composition comprising a compound of Formula (I)
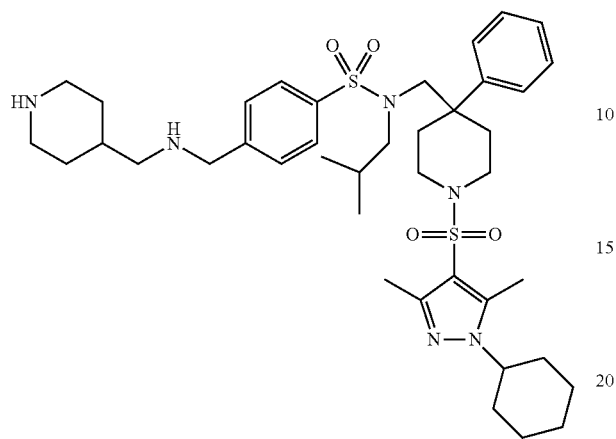
and a pharmaceutically acceptable carrier.